United States Patent
Langstroth et al.

(10) Patent No.: US 7,994,900 B1
(45) Date of Patent: Aug. 9, 2011

(54) MINI-DOME, NURSE CALL VISUAL COMMUNICATION SYSTEM

(75) Inventors: Paul David Langstroth, Pheonix, AZ (US); Charlie Lawrence Peters, Jr., Alamo, CA (US)

(73) Assignee: West-Com Nurse Call Systems, Inc., Fairfield, CA (US)

( * ) Notice: Subject to any disclaimer, the term of this patent is extended or adjusted under 35 U.S.C. 154(b) by 258 days.

(21) Appl. No.: 12/052,912

(22) Filed: Mar. 21, 2008

(51) Int. Cl.
*G08B 5/22* (2006.01)

(52) U.S. Cl. .............. 340/286.07; 340/332; 340/539.12; 705/2

(58) Field of Classification Search ............ 340/286.06–286.08, 573.1, 332, 539.12, 326, 539.1, 311.2; 705/2; 600/300
See application file for complete search history.

(56) References Cited

U.S. PATENT DOCUMENTS

| | | | |
|---|---|---|---|
| 4,237,344 A * | 12/1980 | Moore | 379/38 |
| 4,967,195 A | 10/1990 | Shipley | |
| 5,561,412 A | 10/1996 | Novak et al. | |
| 5,838,223 A | 11/1998 | Gallant et al. | |
| 5,844,488 A | 12/1998 | Musick | |
| 6,693,514 B2 | 2/2004 | Perea, Jr. et al. | |
| 6,781,517 B2 * | 8/2004 | Moster et al. | 340/825.19 |
| 7,092,376 B2 | 8/2006 | Schuman | |
| 7,154,397 B2 | 12/2006 | Zerhusen et al. | |
| 7,292,135 B2 | 11/2007 | Bixler et al. | |
| 2004/0222897 A1 * | 11/2004 | Schuhmann et al. | 340/815.45 |
| 2008/0004904 A1 * | 1/2008 | Tran | 705/2 |
| 2008/0018436 A1 * | 1/2008 | Traughber et al. | 340/286.07 |

* cited by examiner

*Primary Examiner* — Brent Swarthout
(74) *Attorney, Agent, or Firm* — Malin Haley DiMaggio Bowen & Lhota, P.A.

(57) ABSTRACT

A patient and room status display device used to provide effective communication in healthcare environments. The display device uses a RGB (Red, Green and Blue) LED (Light Emitting Diode) to illuminate a dome light with any color, thus providing signals to healthcare workers representing different patient or room statuses. The display device can be operated through an external web-based interface, a nurse call master station or at least one user controlled actuator located on the display device. Each display device is mounted outside of every patient's room to provide multiple status signals for every patient in the hospital wing.

15 Claims, 3 Drawing Sheets

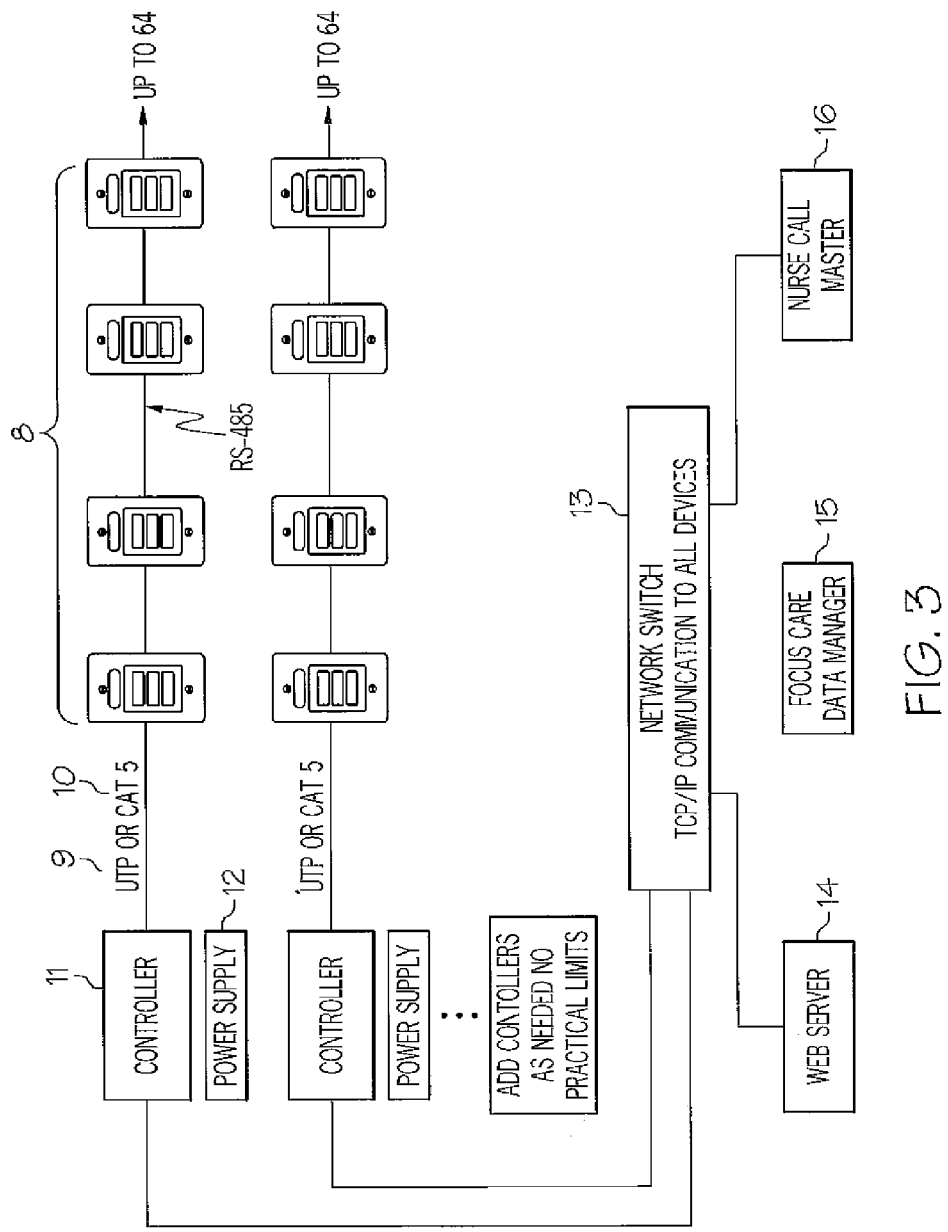

MINI-DOME, NURSE CALL VISUAL COMMUNICATION SYSTEM

CROSS REFERENCE TO RELATED APPLICATIONS

N/A

STATEMENT REGARDING FEDERALLY SPONSORED RESEARCH OR DEVELOPMENT

N/A

BACKGROUND OF THE INVENTION

1. Field of the Invention

The present invention relates to a hospital communication system utilizing individual patient and room status display devices. Specifically, multiple display devices are connected to a local area network allowing each device to be controlled through a variety of different methods and interfaces which update the output status display in real-time.

2. Description of Related Art

Hospital nurses often have to work long hours in a stressful environment. Under such difficult working conditions, effective communication between nurses, patients and doctors is necessary for providing optimal care to patients. Furthermore, clue to increasing costs within the healthcare field, many hospitals use less staff during non-peak hours. Effective communication within the facility is necessary for maximizing the hospital's efficiency when lower staff numbers are used.

One method of improving efficiency through effective communication is with the use of a nurse call system. A nurse call system allows a patient to signal and talk directly to a nurse, who is located at a nurse station. The patient activates a call button that connects the user, through an audio network, to the nurse. The nurse can then respond to the specific needs of the patient by communicating these needs to a nurse located close to the patient. The call button can include other functions such as providing an emergency distress signal or a bathroom signal to the nurse station. Nurse call systems result in an increase in the amount of patient and nurse interaction. This increased interaction provides more information to the nurses, but in turn places more demand on them as they are required to meet even more specific needs of every patient.

Nurse call systems have existed for a number of years and are used in most hospitals. There have been many improvements to these systems in recent years, which allow for an increase in the efficiency of the nurse staff and in the quality of provided care. One such improvement is the use of a packet based communication network. This system allows nurses to handle the multitude of patient calls and identities associated with these calls in an effective manner. Furthermore, the packet based communication network allows for communication with a plurality of secondary audio stations. These audio stations are located throughout the hospital wing and create communication networks between nurses. While the packet based audio network allows for communication amongst nurses from sub stations to a main station, it still requires that roaming nurses check into each sub station to obtain instructions and patient information.

Another method of improving the ease by which health care professionals obtain and respond to patients needs is through the use of a Point-Of-Care computer system. These systems allow doctors, nurses and other hospital staff to access specific information about patients that is stored on a database, from any computer connected to the point-of-care network. Patient data comes from a number of sources including patient monitors, lab results, or information input by hospital workers. These systems provide a more efficient method of storing the large amounts of patient information that are necessary for providing quality healthcare. While the point-of-care system offers an improved means of organizing a wealth of information about each individual patient, computers are still required to access this data. Since it is not cost effective to station a computer in every single room, hospital workers must still effectively communicate the information retrieved through a computer from the database to other staff members.

Improvements made to hospital communication and nurse call systems through packet based networks and point-of-care systems have not only increased the efficiency of communication between patients and hospital staff, but also increased the number of need requests that are handled by the hospital workers. For some complicated patient needs, it is necessary for nurses to check into nurse stations in order to address each patient's requests properly. For other more routine needs, however, the requirement of nurses checking into a station dramatically reduces hospital efficiency. Hospitals now utilize zone lighting to convey signals on the status or needs of corresponding patients. Each lighting unit is placed outside of a patient's room. When the nurse call system is activated, the light illuminates indicating that assistance is needed. The state of the art uses multiple LEDs to create a number of different signals on one zone lighting system. These signals can include a nurse call, the presence of staff in the room, or a "code blue" emergency. The signal to the zone lighting unit can be initiated from a number of sources. These sources include a nurse call button in the patient's room, a pull chain in the patient's room or a central control at the nurse station. Current dome lights provide a much more effective means of communicating simple needs of the patients. Dome lights, however, are limited in the number of signals that can be conveyed. Dome lights usually display only three colors thus drastically limiting the number of different signals that are conveyed. Illumination pattern schemes can be developed by hospitals; however, these become extremely complex and difficult for passing nurses to read.

The present invention offers an improved means of communicating patient and room status to hospital staff through the use of one dome light that is illuminated with a RGB LED. The RGB LED enables any color to be displayed on the device dome light. Furthermore, different colors can be flashed in different patterns to display a number of different cycled signals in a clear and effective manner. The present invention also comprises multiple user controlled actuators. These actuators can be color coordinated to represent any task. The user controlled actuators are operated manually at each display device to illuminate the dome light with the desired status color. Each can be used to convey a number of different messages such as room status or medication reminder. Also, the present invention acts within a nurse call system and can be controlled by either a nurse call master station or a web-based interface system that runs on CAT5 cables. Finally, the present invention is not directly connected to any active monitor, therefore protecting the privacy of the patient while meeting the HIPPA requirements of patient confidentiality.

SUMMARY OF THE INVENTION

The present invention relates to a patient and room status display for use in hospitals to provide a quick and efficient method of communication between hospital staff members by using a single dome light that is capable of creating multiple visible colors. These colors are displayed in a manner that allows them to be cycled, thus displaying multiple status signals. This creates a quick and efficient method for hospital staff passing by the room to determine what the status is of both the room and the patient. The present invention is utilized in combination with a LAN to receive status signals from a web-based interface. Furthermore, the display devices can not only be controlled by a nurse call station, but also generate status messages that are sent back to the nurse call station. The present invention contains a number of user-controlled actuators below the dome light. These buttons can be programmed to initiate communication with the nurse call master station or assigned to represent different status messages.

The dome light is situated on top of the device and illuminated with a RGB (Red Green and Blue) LED. The use of a RGB LED enables the display of any color of visible light in the single dome. LEDs are also much more efficient than normal incandescent light bulbs reducing the amount of power the device consumes. Multiple user controlled actuators are stacked vertically directly below the dome light. These actuators each represent a different status signal color, and are also illuminated through LEDs.

Each display device is mounted outside of every patient room. The display devices are connected in a daisy chain network to multiple controllers. The controllers are each powered with a separate power supply, which also provides power to the display devices. The controller is connected through an IP network to a network switch. The network switch links the controllers to a web server, an XML database and the nurse call master station. The web server provides access to every display device by providing a web interface, which can be accessed from any computer in the network. Users through the web interface generate status signals. These signals are sent through the network switch to the controller. The controller then sends the corresponding signal to the appropriate display device where the proper status is illuminated. The network switch also sends the status signal to the XML database where the status of the display device is stored.

In another embodiment of the present invention, a status message is generated at the nurse call master station and sent to the corresponding display devices in real-time. This message is stored on the XML database and sent through the network switch, to the network controller. The network controller then sends the status signal to the appropriate display device or devices in the chain network, where the proper color is displayed on the dome light to convey the corresponding status message.

In another embodiment of the present invention, a status signal is generated at the display device interface using one of the configurable manual actuators. The signal is then sent from the display device to the controller. The controller sends the signal through an IP based network to a network switch. The corresponding signal is then stored on the XML database and also sent to the nurse call master station. At the nurse call master station, the status of the display device is presented.

It is one object of the present invention to provide a cost effective display device capable of improving communication between hospital workers pertaining to the effective care of each individual patient.

It is another object of the present invention to provide a patient and room status display device that can be controlled through a web-based interface.

It is still another object of the present invention to provide a patient and room status display device that can be controlled though a nurse call station.

It is yet another object of the present invention to provide a patient and room status display device that is controlled with user actuators located on the device.

It is another object of the present invention to provide a patient and room status display device with user actuators that when initiated send a status message that is displayed at the nurse call master station.

These objects and advantages along with others will become evident in the following description and claims as set forth hereinafter.

BRIEF DESCRIPTION OF THE DRAWINGS

FIG. 3 shows the integrated system architecture that is used to control and connect multiple display devices.

DESCRIPTION OF THE PREFERRED EMBODIMENTS

The present invention relates to patient and room status displays for use in hospitals or other healthcare environments. Each display unit contains a dome light that is capable of being illuminated with any color. Each color represents a different status signal, which is used by hospital staff to determine the needs and tasks required to provide optimal health care to each individual patient. The display unit also contains multiple user configurable actuators, which are operated at the actual unit display interface. Each configurable actuator is used to either control the status message that is displayed on the dome light or to send a status message to the nurse call master station.

Figure 1:
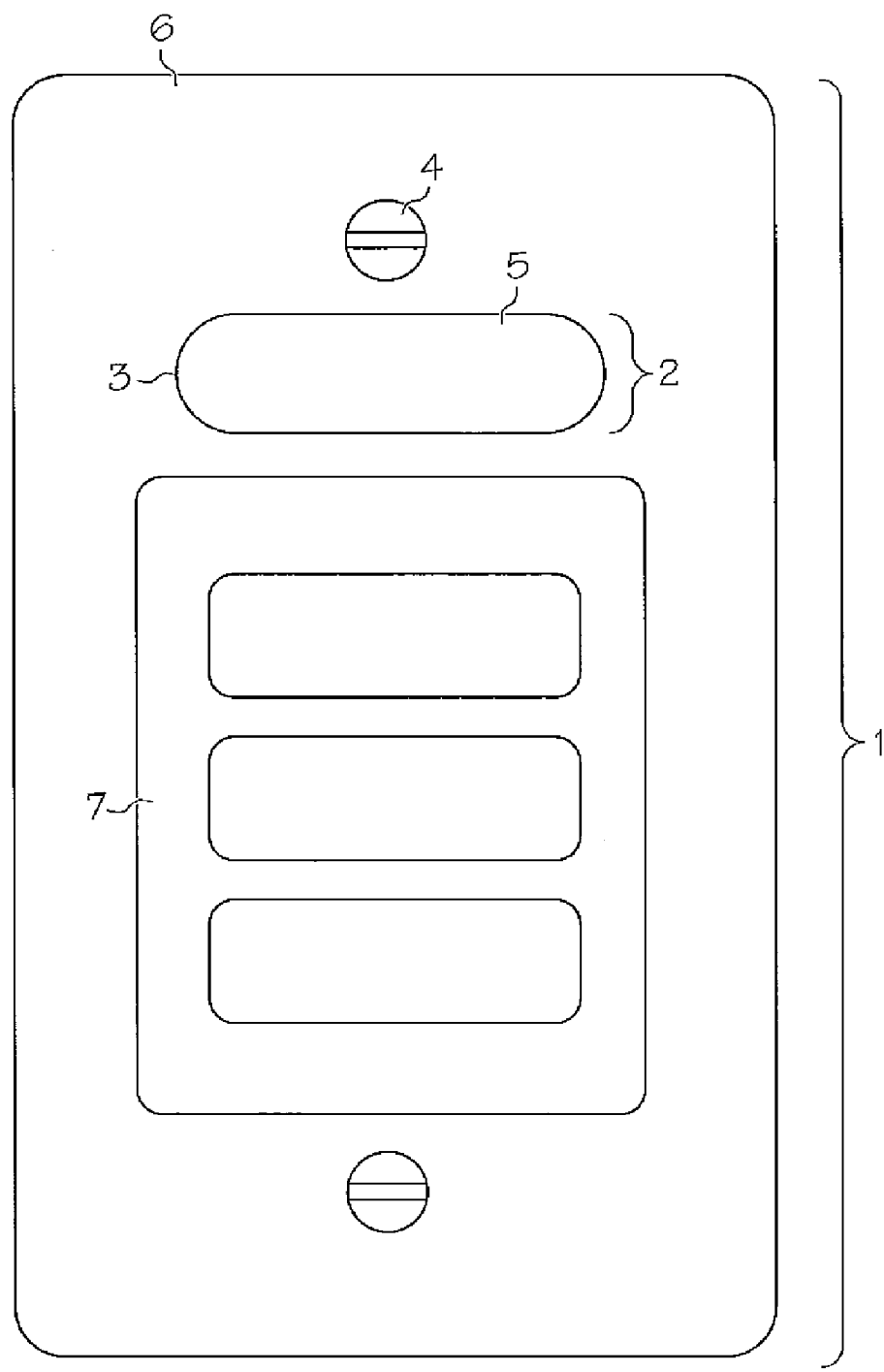
FIG. 1 is a topographical view of the outer face of the patient and room status display device

FIG. 1. is a topographical view of the outer face of the patient and room status display device 1. The entire assembly is encased within a plastic housing 6, which is mounted on to the wall outside of each patient's room using screws 4 in a manner similar to the attachment of a light switch. The dome light 2 is located near the top of the plastic face 6. The dome light 2 comprises a thin lens 3 made out of a reflective material. The thin lens 3 encases a RGB LED 5. Below the dome light 2, surrounded by the plastic housing 6, are multiple user controlled actuators 7.

Figure 2:
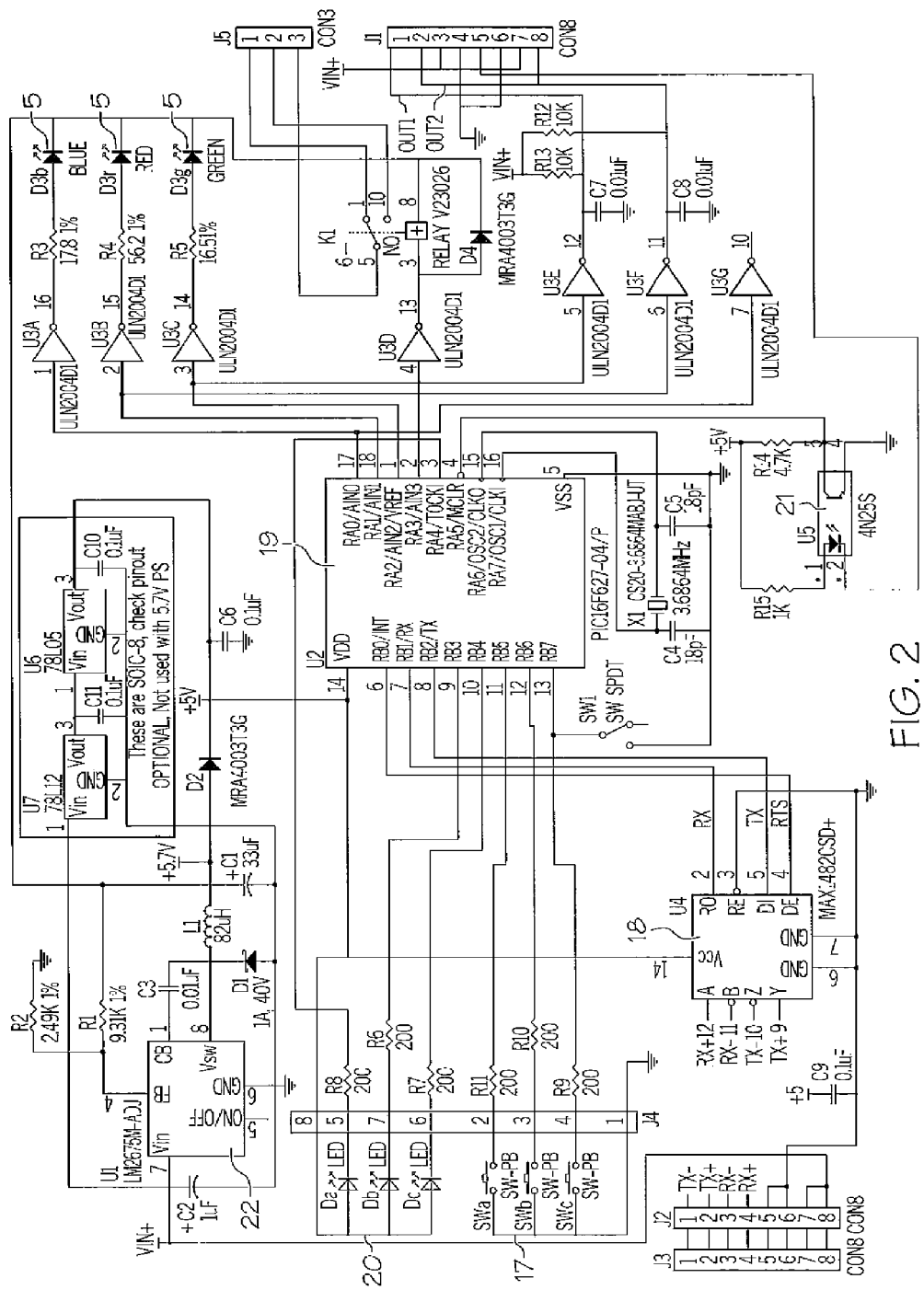
FIG. 2 is a schematic of the room status and display device circuitry

FIG. 2. is a schematic of the circuitry that is used to control and operate the functioning of the display device 1. Multiple push switches 17 are used as the user controlled actuators 7. Upon activation of a push switch 17, a current flows to the corresponding actuator LED 20, causing the actuator button to illuminate. A RGB LED 5 is located on the printed circuit board and are used to illuminate the dome light 2. The entire display device is operated with an 8-bit micro controller 19. This micro controller 19 uses CMOS based flash memory, upgradeable firmware, a watch-dog timer and an RS-485 UART (universal asynchronous receiver/transmitter). The watch-dog timer enables a timing function to be added to the device in correlation with the user-controlled actuators 7.

In one embodiment of the present invention, the user-controlled actuator 7 is activated. This causes the corresponding push switch 17 to allow current to flow to the corresponding actuator LED 20 causing it to illuminate. The activation of the push switch 17 also allows a signal to flow to the micro controller 19. The micro controller 19 sends receives the signal and sends a signal to the RGB LED 5 corresponding to the received signal. This causes the RGB LED 5 to emit light at a specific visible wavelength based upon the current level in the signal sent from the micro controller 19. A switching regulator 22 is used to step down the input voltage. The circuit board is located behind the control panel. The light emitted from the RGB LED 5 is transmitted into the multicolor dome light from the circuit board through a plastic optical fiber. The individual actuator LEDs 20 are located within the push switches 17 on the control panel. The actuator LEDs 20 and the push switches 17 are connected to the circuit board through an 8 channel input/output contech connector.

In another embodiment of the present invention, an RS-485 transceiver 18 receives a signal from the system controllers 11 which are connected through an RS-485 network. The signal is sent to the micro controller 19. The micro controller 19 receives the signal and sends a corresponding signal at specific current levels to the RGB LED based upon the received signal. The RGB LED 5 emits light in response to the amount of current that is applied by the micro controller 11. The RGB LED 5 is capable of emitting any color of visible light. The dome light 2 becomes illuminated providing a quick and effective manner of communicating the status of either the patient or the room In another embodiment of the present invention, multiple signals are input into the display device 1. These signals are sent through the RS-485 transceiver 18 to the micro controller 19. The micro controller 19 stores each signal through flash memory. The micro controller 19 then sends a corresponding signal for each received signal causing the RGB LED 5 to emit a unique color of light representing a different status. The micro controller 19 uses flash memory to continue sending signals in the same pattern. The RGB LED 5 changes colors in response to every signal in a cyclical pattern. This creates an efficient means of communicating multiple statuses to the hospital staff. These statuses can include but are not limited to fall risk, no prescriptions orally, isolation, pain medication reassessment timer elapsed, bed is operating correctly/incorrectly, and room needs to be cleaned/is clean/ requires repair.

FIG. 3 shows the system architecture of various control interfaces coupled with multiple patient and room status display devices. In this system, multiple display devices 8 are connected in a daisy chain network configuration. The multiple display devices 8 are connected to the controller 11 through a RS-485 network. The advantageous of using a RS-485 network is a substantial reduction in the amount of noise present in the signals. This allows for signal communication between individual display device 1 over larger distances and at faster speeds. Connections between multiple display devices 8 and multiple controllers 11 are made through either UTP 9 or CAT 5 10 cables. A power supply 12 provides power to the each individual controller 11 and to each individual display device 1 in the RS-485 network. The controllers 11 are connected to a network switch 13. The network switch connects a web server 14, a data manager XML database 15 and the nurse call master station 16. The web server 14, data manager XML database 15 and nurse call master station 16 are connected through the network switch to the controller 11 through an IP based network. The information is sent between the controllers 11 in UDP data packets.

The web server 14 provides a web-based interface, which can be accessed from any computer in the network. The web server 14 is utilized to make real-time status changes to the display devices. The XML database 15 stores data on each individual display device 1 in the network. The use of an XML database 15 provides an efficient method of storing the data that is transmitted through the network. The connection to the nurse call master station 16 provides a link in communication between the display devices 8 and the nurse call station 16. The nurse call station 16 can be used to control and send status messages in real-time to be presented on the patient and room status display devices 8. Likewise status messages can be generated at the display device 8 and then sent to the nurse call station 16 and displayed in real-time.

In another embodiment of the present invention, a user initiates a real-time status change through the web server 14 through any web interface that is located on the network. The status change creates a signal, which is sent to the network switch 13. The signal is then sent to the XML database where the change in the status of display device 1 is stored. The signal is sent from the network switch 13 to the controller 11. The controller then sends a status signal corresponding to the input signal through the RS-485 network, to the appropriate display device 1 through either UTP 9 or CAT 5 10 cables. The status signal causes the RGB LED 5 to emit light of a specific color based upon the specified status that the input signal represents. This causes the dome light 2 to illuminate providing a signal to hospital staff on the patient or room status.

In another embodiment of the present invention, a user initiates a real-time status change through a user-controlled actuator 7 located on the display device 1. This status change is limited to non-patient safety issues such as the room status or a pain check reminder. This status change creates a signal that is then transmitted to the RGB LED 5 causing it to emit a specific color of light. The dome light 2 is illuminated with the light from the RGB LED 5. The status change signal is sent to the controller 11 through either UTP 9 or CAT 5 10 cables in the RS-485 network. The signal is sent from the controller 11 to the IP based network switch 13. The switch then transfers the signal to the nurse call master station 16. The signal initiates an event in the nurse call system. For example, a caregiver pushes the actuator representing the event to check pain medication. This initiates a timer function in the display device through the use of a watch-dog timer. Once the timer expires, a signal is sent in real-time to the nurse call master station warning that the time between checking pain medication has expired. The nurse call system, in turn, notifies a caregiver through a messaging device to check the pain medication on a specific patient. Once the caregiver has finished checking the pain medication, the actuator is pushed again, and the process starts all over.

In another embodiment of the present invention, the display device 1 is used to show the status of an ancillary device that is not directly related to patient care. An example of an ancillary device is an integrated bed system. The display device 1 can be used to display statuses from the bed system such as wheels not locked or rail down. The ancillary device is coupled directly to the display device 1. A signal is sent to the display device 1 which causes the RGB LED 5 to emit light of a specific color. This in turn causes the dome light 2 to illuminate.

The present invention is not limited to the specific embodiments described above. Many different embodiments that are not described exist without departing significantly from the scope or the spirit of the present invention. The described embodiments thus serve as examples of the present invention and are not restrictive of the scope of the invention.

What is claimed is:

1. A method for communicating status information using an illuminating status display device comprising the steps of providing at least one display device, each having a light producing element capable of displaying a plurality of colors and at least one actuator, where each said actuator is electrically connected to the same light producing element;

providing a plurality of distinct visual outputs, where each said visual output communicates a different nurse call status message through the light producing element;

providing a plurality of distinct electronic status change signals, where each said status change signal represents one status message and is associated with one corresponding visual output on said light producing element such that the transmission of any status change signal to the light producing element causes the display of the that status change signal's corresponding visual output on the light producing element, each actuator being associated with a distinct status change signal such that manual input to the actuator causes the actuator's associated status change signal to be transmitted to the light producing element, and the same light producing element being capable of displaying the associated visual output of any status change signal;

electronically connecting each said display device to a controller, said controller being connected to an electronic data transfer network;

generating at least one of said status change signal through a web interface associated with a computer connected to said network;

causing said status change signal to be transmitted from the computer across said network to a network switch and from said network switch to said controller; and said controller sending said status change signal to the light producing element of at least one of said display devices, causing said light producing element to display the associated visual output.

2. The method of claim 1, where each said distinct visual output comprises a distinct light color.

3. The method of claim 1, further comprising the step of transmitting the status change signal from said network switch to a database for storage.

4. The method of claim 3, wherein the database is an XML.

5. The method of claim 1, wherein the light producing element is a unitary RGB LED.

6. The method of claim 1, wherein said status messages include patient status information, room status information, and equipment status information, said patient status information including at least data concerning patient fall risk, oral prescriptions, isolation, and pain medication, said room status information including at least data concerning room cleaning and room servicing, and said equipment status information including at least information concerning bed operation.

7. The method of claim 1, wherein said display device additionally has a dome light and an internal controller, where said internal controller can cause the light producing element in the same display device as the internal controller to emit a desired color of light and utilizes a data storage element and a timing element, said dome light comprising a thin lens made of translucent reflective material, and any light emitted from said light producing element is transmitted into the dome light though an optical fiber.

8. The method of claim 7, wherein said internal controller stores one or more status change signals received on said data storage element in the order received and causes the light producing element housed in the same display device to automatically replicate the display of the associated visual output of the one or more status change signals stored in the data storage element after a predetermined time period that is tracked by the timing element.

9. A method for communicating status information using an illuminating a status display device comprising the steps of providing at least one display device having a light producing element capable of displaying a plurality of colors, and at least one actuator, where each said actuator is electrically connected to the same light producing element;

providing a plurality of distinct visual outputs, where each said visual output communicates a different nurse call status message through the light producing element;

providing a plurality of distinct electronic status change signals, where each said status change signal represents one status message and is associated with one corresponding visual output on said light producing element, such that the transmission of any status change signal to the light producing element causes the display of the that status change signal's corresponding visual output on the light producing element, each actuator being associated with a distinct status change signal such that manual input to the actuator causes the actuator's associated status change signal to be transmitted to the light producing element, and the same light producing element being capable of displaying the associated visual output of any status change signal;

electronically connecting each said display device to a controller, said controller being connected to an electronic data transfer network;

providing a master station capable of generating new status change signals and terminating existing status change signals;

connecting said master station to the electronic network;

generating at least one of said status change signals through said master station;

causing said status change signal to be transmitted from said master station to a network switch and from said switch to a database for storage and said controller;

receiving and storing the status change signal on the database;

receiving the status message at the controller; and transmitting the status change signal from the controller to the said light producing element of at least one of display devices, causing said light producing element to display the associated visual output.

10. The method of claim 9, wherein said visual output comprises at least one distinct light color; and the light producing, element is an RGB LEDs.

11. The method of claim 9, wherein said master station includes a graphical user interface; and the status message associated with the status change signal transmitted from the master station is displayed on the graphical user interface.

12. The method of claim 9, wherein the database is an XML database.

13. The method of claim 9, wherein said status messages comprise patient status information, room status information, and equipment status information, said patient status information including at least data concerning patient fall risk, oral prescriptions, isolation, and pain medication, said room status information including at least data concerning room cleaning and room servicing, and said equipment status information including at least information concerning bed operation.

14. The method of claim 9, wherein display device additionally has a dome light and an internal controller, where said internal controller can cause the light producing element in the same display device as the internal controller to emit a desired color of light and utilizes a data storage element and a timing element, said dome light comprising a thin lens made of translucent reflective material, and any light emitted from said light producing element is transmitted into the dome light though an optical fiber.

15. The method of claim 14, wherein internal controller stores one or more status change signals received on said data storage element in the order received and causes the light producing element housed in the same display device to automatically replicate the display of the associated visual output of the one or more status change signals stored in the data storage element after a predetermined time period that is tracked by the timing element.

* * * * *